US008772271B2

(12) United States Patent
Nagi et al.

(10) Patent No.: US 8,772,271 B2
(45) Date of Patent: *Jul. 8, 2014

(54) MICRONIZED TANAPROGET, COMPOSITIONS, AND METHODS OF PREPARING THE SAME

(71) Applicant: Wyeth LLC, Madison, NJ (US)

(72) Inventors: Arwinder S. Nagi, Moorpark, CA (US); Ramarao Chatlapalli, Hopewell Junction, NY (US); Shamim Hasan, East Elmhurst, NY (US); Mohamed Ghorab, West Lafayette, IN (US); Dhaval Gaglani, Edison, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/890,523

(22) Filed: May 9, 2013

(65) Prior Publication Data

US 2013/0251807 A1 Sep. 26, 2013

Related U.S. Application Data

(63) Continuation of application No. 12/752,520, filed on Apr. 1, 2010, now Pat. No. 8,450,312, which is a continuation of application No. 11/411,523, filed on Apr. 26, 2006, now Pat. No. 7,767,668.

(60) Provisional application No. 60/675,550, filed on Apr. 28, 2005.

(51) Int. Cl.
*A61K 31/335* (2006.01)
*A61K 31/56* (2006.01)
*C07D 295/00* (2006.01)
*C07D 265/12* (2006.01)

(52) U.S. Cl.
USPC .............................. 514/170; 544/70; 544/92

(58) Field of Classification Search
USPC ...................................... 514/170; 544/70, 92
See application file for complete search history.

(56) References Cited

U.S. PATENT DOCUMENTS

| | | | |
|---|---|---|---|
| 6,436,929 B1 | 8/2002 | Zhang | |
| 7,081,457 B2 | 7/2006 | Zhang | |
| 7,192,956 B2 | 3/2007 | Fensome | |
| 7,268,149 B2 | 9/2007 | Fensome | |
| 7,317,037 B2 | 1/2008 | Fensome | |
| 7,496,489 B2 | 2/2009 | Olland | |
| 7,569,564 B2 | 8/2009 | Zhang | |
| 7,569,679 B2 | 8/2009 | Shen | |
| 7,572,779 B2 | 8/2009 | Aloba | |
| 7,582,755 B2 | 9/2009 | Wilk | |
| 7,759,341 B2 | 7/2010 | Tesconi | |
| 7,767,668 B2 * | 8/2010 | Nagi et al. .................. 514/230.5 |
| 7,786,297 B2 | 8/2010 | Chatlapalli | |
| 7,968,709 B2 | 6/2011 | Tesconi | |
| 8,114,869 B2 | 2/2012 | Tesconi | |
| 8,343,965 B2 * | 1/2013 | Nagi et al. .................. 514/230.5 |
| 8,450,312 B2 * | 5/2013 | Nagi et al. .................. 514/230.5 |
| 8,513,240 B2 * | 8/2013 | Nagi et al. .................. 514/230.5 |
| 2003/0092711 A1 | 5/2003 | Zhang | |
| 2004/0265355 A1 | 12/2004 | Shalaby | |
| 2006/0009428 A1 | 1/2006 | Grubb | |
| 2006/0030615 A1 | 2/2006 | Fensome | |
| 2006/0035843 A1 | 2/2006 | Shen | |
| 2006/0246128 A1 | 11/2006 | Nagi | |
| 2006/0246135 A1 | 11/2006 | Nagi | |
| 2006/0247234 A1 | 11/2006 | Nagi et al. | |
| 2006/0247235 A1 | 11/2006 | Tesconi | |
| 2006/0247236 A1 | 11/2006 | Chatlapalli | |
| 2006/0280800 A1 | 12/2006 | Nagi | |
| 2011/0091539 A1 | 4/2011 | Nagi | |
| 2012/0114748 A1 | 5/2012 | Nagi | |
| 2012/0115858 A1 | 5/2012 | Tesconi | |
| 2013/0142838 A1 | 6/2013 | Nagi | |

FOREIGN PATENT DOCUMENTS

| | | |
|---|---|---|
| JP | 2002-543192 | 12/2002 |
| JP | 2005-535624 | 11/2005 |
| JP | 2005-535628 | 11/2005 |
| JP | 2007-534760 | 11/2007 |
| JP | 2007-534767 | 11/2007 |
| JP | 2008-505909 | 2/2008 |
| JP | 2008-509216 | 3/2008 |
| JP | 2008-509217 | 3/2008 |

(Continued)

OTHER PUBLICATIONS

Fensome, "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonists Tanaproget" J. Med. Chem., 48:5092-5095 (Jul. 12, 2005).

(Continued)

*Primary Examiner* — Ali Soroush
(74) *Attorney, Agent, or Firm* — Howson & Howson LLP

(57) ABSTRACT

The present invention provides compositions, desirably pharmaceutical compositions, containing micronized tanaproget. The compositions can also contain microcrystalline cellulose, croscarmellose sodium, anhydrous lactose, magnesium stearate, micronized edetate calcium disodium hydrous, and micronized sodium thiosulfate pentahydrate. The compositions are useful in contraception and hormone replacement therapy and in the treatment and/or prevention of uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors, and in the preparation of medicaments useful therefor. Additional uses include stimulation of food intake.

38 Claims, No Drawings

(56) References Cited

FOREIGN PATENT DOCUMENTS

| JP | 2008-509917 | 4/2008 |
|---|---|---|
| JP | 2008-510722 | 4/2008 |
| JP | 2008-539254 | 11/2008 |
| JP | 2008-539258 | 11/2008 |
| JP | 2008-539262 | 11/2008 |
| JP | 2008-539264 | 11/2008 |
| WO | WO-04/000801 | 12/2003 |
| WO | WO-2005/104711 | 11/2005 |
| WO | WO-2005/105817 | 11/2005 |
| WO | WO-2006/014476 | 2/2006 |

OTHER PUBLICATIONS

Zhang, "Novel 6-Aryl-1,4-dihydrobenzo[d][1,3]oxazine-2-thiones as Potent, Selective, and Orally Active Nonsteroidal Progesterone Receptor Agonists", Bioorg. & Med. Chem. Lett., 13:1313-1316 (Apr. 7, 2003).
Winneker, "Nonsteroidal Progesterone Receptor Modulators: Structure Activity Relationships" Sem. in Reprod. Med., 23(1):46 (2005).
Bapst, "Clinical Pharmacokinetics of Tanaproget, A Non-Steroidal Progesterone Receptor (PR) Agonist, in Healthy Cycling Women During 28 Days of Administration", Am. Soc. for Clin. Pharmacol. Ther., Abstract PI-138, (Feb. 2005), p. 44.
Crabtree, "Development of a Mouse Model of Mammary Gland Versus Uterus Tissue Selectivity Using Estrogen- and Progesterone-Regulated Gene Markers", J. Steroid Biochem. & Mol. Biol., 101:11-21, (Sep. 2006; e-published Aug. 22, 2006).
Bapst, "Pharmacokinetics and Safety of Tanaproget, a Nonsteroidal Progesterone Receptor Agonist, in Healthy Women", Contraception, 74:414-418 (Nov. 2006; e-published Sep. 15, 2006).
Bruner-Tran, "Down-Regulation of Endometrial Matrix Metalloproteinase-3 and -7 Expression in Vitro and Therapeutic Regression of Experimental Endometriosis in Vivo by a Novel Nonsteroidal Progesterone Receptor Agonist, Tanaproget", J. Clin. Endocrinol. & Metab/, 91(4):1554-1560 (Apr. 2006; e-published Jan. 17, 2006).
Nazzal, "Effect of Extragranular Microcrystalline Cellulose on Compaction, Surface Roughness, and in vitro Dissolution of a Self-nanoemulsified Solid Dosage Form of Ubiquinone", Pharm. Tech., 26(4):86-89 (Apr. 1, 2002)—Abstract.
Li, "The Role of Intra- and Extragranular Microcrystalline Cellulose in Tablet Dissolution", Pharm. Dev. Tech., 1(4):343-355 (Dec. 1996)—Abstract.
Shotton and Leonard, "Effect of Intragranular and Extragranular Disintegrating Agents on Particle Size of Disintegrated Tablets", J. Pharm. Sci., 65(8):1170-1174 (Aug. 1976)—Abstract.
Borka, "Crystal Polymorphism of Pharmaceuticals", Acta Pharm. Jugoslavica, 40:71-94 (1990).
Mitsuru, "Keiko-Toyo-Seizai no Sekkyei to Hyoka", Yakugyo Jiho, Inc., pp. 81-85, Japan (1995).
Japan Pharmaceutical Excipients Council Ed., "Iyakuhin-Tenkabutsu Jiten", Yakuji Nippo Limited, pp. 17, 46, 49, 72, 82, 124, 133, 144, and 214, Japan (Jan. 14, 1994.
International Search Report and Written Opinion dated Oct. 16, 2006 corresponding to related International Patent Application No. PCT/US2006/015837.
International Search Report and Written Opinion dated Oct. 16, 2006 corresponding to related International Patent Application No. PCT/US2006/016020.
International Search Report and Written Opinion dated Oct. 16, 2006 corresponding to related International Patent Application No. PCT/US2006/015813.
International Search Report and Written Opinion dated Oct. 16, 2006 corresponding to related International Patent Application No. PCT/US2006/015852.
Office Action dated Dec. 17, 2009 and issued in U.S. Appl. No. 11/412,022.
Applicant's Response to the Office Action dated Dec. 17, 2009 and issued in U.S. Appl. No. 11/412,022.
Office Action dated Sep. 18, 2009 and issued in U.S. Appl. No. 11/412,014.
Applicant's Response to the Office Action dated Sep. 18, 2009 and issued in U.S. Appl. No. 11/412,014.
Office Action dated Apr. 16, 2010 and issued in U.S. Appl. No. 11/412,014.
Office Action dated Nov. 12, 2008 and issued in U.S. Appl. No. 11/412,016.
Applicant's Response to the Office Action dated Nov. 12, 2008 and issued in U.S. Appl. No. 11/412,016.
Office Action dated Aug. 19, 2009 and issued in U.S. Appl. No. 11/412,016.
Applicant's Response to the Office Action dated Aug. 19, 2009 and issued in U.S. Appl. No. 11/412,016.
Office Action dated Apr. 29, 2010 and issued in U.S. Appl. No. 11/412,016.
Office Action dated Apr. 2, 2009 and issued in U.S. Appl. No. 11/412,015.
Applicant's Response to the Office Action dated Apr. 2, 2009 and issued in U.S. Appl. No. 11/412,015.
Office Action dated Oct. 1, 2008 and issued in U.S. Appl. No. 11/411,523.
Applicant's Response to the Office Action dated Oct. 1, 2008 and issued in U.S. Appl. No. 11/411,523.
Office Action dated Mar. 4, 2009 and issued in U.S. Appl. No. 11/411,523.
Applicant's Response to the Office Action dated Mar. 4, 2009 and issued in U.S. Appl. No. 11/411,523.
Office Action dated Feb. 13, 2012 issued in related Indian Patent Application No. 4106/KOLNP/2007.
Office Action dated Jan. 31, 2012 issued in related Japanese Patent Application No. 2008-509087.
Office Action dated Jul. 22, 2010 issued in related U.S. Appl. No. 11/412,022.
Office Action dated Oct. 3, 2012 issued in related U.S. Appl. No. 12/975,444.
Applicant's Response to the Office Action dated Oct. 3, 2012 issued in related U.S. Appl. No. 12/975,444.
Applicant's Response to the Office Action dated Apr. 16, 2010 issued in related U.S. Appl. No. 11/412,014.
Applicant's Response to the Office Action dated Apr. 29, 2010 issued in related U.S. Appl. No. 11/412,016.
Office Action dated Nov. 27, 2009 issued in related U.S. Appl. No. 11/412,015.
Applicant's Response to the Office Action dated Nov. 27, 2009 issued in related U.S. Appl. No. 11/412,015.
Office Action dated Jan. 5, 2011 issued in related U.S. Appl. No. 12/792,978.
Applicant's Response to the Office Action dated Jan. 5, 2011 issued in related U.S. Appl. No. 12/792,978.
Office Action dated Sep. 18, 2012 issued in related U.S. Appl. No. 12/752,520.
Applicant's Response to the Office Action dated Sep. 18, 2012 issued in related U.S. Appl. No. 12/752,520.
English translation of an Office Action dated Nov. 26, 2013 issued in related Japanese Patent Application No. 2012-169771.

\* cited by examiner

MICRONIZED TANAPROGET, COMPOSITIONS, AND METHODS OF PREPARING THE SAME

BACKGROUND OF THE INVENTION

Intracellular receptors (IR) form a class of structurally related gene regulators known as "ligand dependent transcription factors". The steroid receptor family is a subset of the IR family, including the progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the cell membrane via passive diffusion, and binds to the IR to create a receptor/ligand complex. This complex binds to specific gene promoters present in the cell's DNA. Once bound to the DNA, the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control compositions, typically in the presence of an ER agonist, alternatively they may be used in conjunction with a PR antagonist. ER agonists are used to treat the symptoms of menopause, but have been associated with a proliferative effect on the uterus which can lead to an increased risk of uterine cancers. Co-administration of a PR agonist reduces/ablates that risk.

Tanaproget, 5-(4,4-dimethyl-2-thioxo-1,4-dihydro-2H-3, 1-benzoxazin-6-yl)-1H-methyl-pyrrole-2-carbonitrile, is a progesterone receptor modulator and is effective in contraception, hormone replacement therapy, and treating carcinomas and adenocarcinomas, dysfunctional bleeding, uterine leiomyomata, endometriosis, and polycystic ovary syndrome.

What is needed in the art are compositions containing tanaproget for administration to a mammalian subject.

SUMMARY OF THE INVENTION

In one aspect, the present invention provides compositions containing micronized tanaproget or a pharmaceutically acceptable salt thereof, microcrystalline cellulose, croscarmellose sodium, anhydrous lactose, magnesium stearate, micronized edetate calcium disodium hydrous, and micronized sodium thiosulfate pentahydrate.

In still a further aspect, the present invention provides processes for preparing compositions containing micronized tanaproget.

Other aspects and advantages of the present invention are described further in the following detailed description of the preferred embodiments thereof.

DETAILED DESCRIPTION OF THE INVENTION

The present invention provides effective pharmaceutical compositions containing micronized tanaproget. The micronized tanaproget can be readily formulated into an oral dosage unit, and is particularly well suited for a directly compressible unit. The inventors have found that tablets or caplets prepared by direct compression of or capsules containing the micronized tanaproget compositions of the invention exhibited rapid and complete drug release, as compared to non-micronized tanaproget. Thus, the compositions of the invention provide for fast drug release.

Briefly, tanaproget is micronized under nitrogen and conventional micronizing techniques, for example with a Trost or jet mill, applied to non-micronized tanaproget. One method of preparation of non-micronized tanaproget is described in U.S. Pat. No. 6,436,929, and generally in US Patent Application Publication No. 2005/0272702, published Dec. 8, 2005. However, the invention is not limited to the method by which the non-micronized tanaproget is produced.

In another embodiment, non-micronized tanaproget is purified by recrystallization. In one embodiment, non-micronized tanaproget is recrystallized from acetone and water. In a further embodiment, the tanaproget is dissolved in acetone, the acetone solution heated, water added to the heated acetone solution, and the acetone/water solution cooled to provide purified tanaproget. This purification specifically includes dissolving crude tanaproget in acetone and heating the solution to about 45 to about 51° C. After circulating the heated solution through a carbon filter for at least about 4 hours, the filtered solution was concentrated using procedures known to those of skill in the art. After adding water to the concentrated solution, in one embodiment at a rate which does not cool the refluxing acetone solution, the acetone/water solution was cooled to about −6 to about 0° C. In one embodiment, the acetone/water solution was cooled at a rate of less than about 0.5° C./minute. After holding the batch at the reduced temperature for at least about 3 hours, the precipitated, purified tanaproget is collected using filtration. The collected solid is washed with a water/acetone mixture, in one embodiment washed twice with a 1:1 water/acetone mixture. The washed purified tanaproget is then dried at less than 35° C. for about 4 hours. Further drying at less than about 50° C. was performed to remove residual acetone/water as measured by spectroscopic methods.

In one embodiment, micronized tanaproget prepared according to the present invention has a particle size of less than about 20 μm, less than about 15 μm, or less than about 10 μm. In a further embodiment, 90% of the particles are less than or equal to about 20 μm and 50% are less than or equal to about 15 μm as determined by the Malvern method, which is readily understood by one of skill in the art.

The micronized tanaproget encompasses tautomeric forms of tanaproget and salts derived from pharmaceutically or physiologically acceptable acids, bases, alkali metals and alkaline earth metals. The present invention also includes derivatives of tanaproget, including, but not limited to, esters, carbamates, sulfates, ethers, oximes, carbonates, and the like.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates.

These salts, as well as the nonmicronized and micronized tanaproget can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

Micronized tanaproget discussed herein also encompasses "metabolites" which are unique products formed by processing tanaproget by the cell or patient. In one embodiment, metabolites are formed in vivo.

In one embodiment, the compositions of the invention are prepared by dry mixing micronized tanaproget, based upon the total weight of the unit dose, with the other components of the composition. In another embodiment, the compositions of the invention are prepared by wet mixing micronized tanaproget, based upon the total weight of the unit dose, with the other components of the composition.

As referred to herein below, the term "wt/wt" refers to the weight of one component based on the total weight of the components utilized in the composition. In one embodiment, wt/wt refers to the weight of one component based on the total weight of the composition. In another embodiment, wt/wt refers to the weight of one component based on the total weight of the final tablet or caplet. In one embodiment, this ratio does not include the weight of the capsule, the weight of any filler utilized in the capsule, and seal coating, if so utilized.

A. The Composition of the Invention

The compositions of the present invention are formulated to provide rapid release of tanaproget, while simultaneously being stable under conditions of storage. In one embodiment, the composition contains micronized tanaproget, or a pharmaceutically acceptable salt thereof, microcrystalline cellulose (MCC), croscarmellose sodium, anhydrous lactose, magnesium stearate, micronized edetate calcium disodium hydrous (EDTA), and micronized sodium thiosulfate pentahydrate. In a further embodiment, the tanaproget is intragranular. In still a further embodiment, the tanaproget, MCC, anhydrous lactose, EDTA, and sodium thiosulfate pentahydrate are intragranular.

In one embodiment, micronized tanaproget is present in the composition of the invention in an amount from 0.15% to about 0.50% wt/wt of the composition. This amount may be varied, depending upon the amount of micronized tanaproget to be delivered to a patient. The desired therapeutic regimen can be taken into consideration when formulating the composition of the invention. In another embodiment, an overage of tanaproget is utilized, e.g., a 5% overage. For example, micronized tanaproget is present in the formulation at about 0.15% wt/wt based upon the total weight of the unit dose. In another example, micronized tanaproget is present in the composition at about 0.23% wt/wt based upon the total weight of the unit dose. In a further example, micronized tanaproget is present in the composition at about 0.31% wt/wt based upon the total weight of the unit dose. In yet another example, micronized tanaproget is present in the composition at about 0.5% wt/wt based upon the total weight of the unit dose.

The composition also includes microcrystalline cellulose (MCC), in one embodiment at about 30 to about 50% wt/wt of the composition. In one example, MCC is present in the composition at about 30% wt/wt. In another example, MCC is present in the composition at about 40% wt/wt. In a further example, MCC is present in the composition at about 50% wt/wt.

The composition also includes croscarmellose sodium, in one embodiment at about 2 to about 6% wt/wt of the composition, in extragranular and/or intragranular forms. In one example, croscarmellose sodium is present at about 2% wt/wt of the composition. In another example, croscarmellose sodium is present at about 4% wt/wt of the composition. In a further example, croscarmellose sodium is present at about 6% wt/wt of the composition.

The composition further includes one or more of an "antioxidant". By the term "antioxidant" is meant a compound that is capable or inhibiting or retarding the degradation of the composition of the present invention. In one embodiment, the antioxidant inhibits or retards the degradation of the tanaproget in the composition. Examples of antioxidants that are useful in the present invention include sodium thiosulfate, sodium metabisulfite, cysteine, methionine, vitamin E, and edetate calcium disodium hydrous (EDTA). In a further embodiment, the antioxidant is micronized prior to use in the present invention.

In one embodiment, the compositions of the invention include EDTA, which is present at about 0.05 to 0.15% wt/wt of the composition, or about 0.05, 0.10, or 0.15% wt/wt of the composition. In one embodiment, the EDTA is micronized and 90% of the particles are less than or equal to about 35 µm, 50% are less than or equal to about 11 µm, and 10% are less than or equal to 3 µm as determined by the Malvern method, which is readily understood by one of skill in the art.

In one embodiment, sodium thiosulfate pentahydrate is present in the composition at about 0.25 to about 0.75% wt/wt, or about 0.25, 0.50 (or 0.5), or 0.75% wt/wt. In one embodiment, the sodium thiosulfate pentahydrate is micronized and 90% of the particles are less than or equal to about 31 µm, 50% are less than or equal to about 13 µm, and 10% are less than or equal to 4 µm as determined by the Malvern method, which is readily understood by one of skill in the art.

In one example, the composition includes EDTA at about 0.25% wt/wt and sodium thiosulfate at about 0.25% wt/wt. In another example, the composition includes EDTA at about 0.10% wt/wt and sodium thiosulfate at about 0.50% wt/wt. In a further example, the composition includes EDTA at about 0.15% wt/wt and sodium thiosulfate at about 0.75% wt/wt.

The composition of the invention also includes anhydrous lactose, typically at about 54 to about 55% wt/wt of the composition. In one example, anhydrous lactose is present at about 54% wt/wt of the composition. In a further example, anhydrous lactose is present at about 55% wt/wt of the composition. In another example, anhydrous lactose is present at about 54.8% wt/wt of the composition. In a further example, anhydrous lactose is present at about 54.79% wt/wt of the composition. In still another example, anhydrous lactose is present at about 54.71% wt/wt of the composition. In yet a further example, anhydrous lactose is present at about 54.56% wt/wt of the composition.

The composition of the invention further includes magnesium stearate, in one embodiment at about 0.25 to about 0.5% wt/wt. In a further embodiment, the composition contains about 0.25% wt/wt of magnesium stearate. In another embodiment, the composition contains about 0.375% wt/wt of magnesium stearate. In another embodiment, the composition contains about 0.5% wt/wt of magnesium stearate. In still another embodiment, the composition contains about 0.37% wt/wt of magnesium stearate. The magnesium stearate can be present in intragranular and/or extragranular forms.

In one embodiment, a composition of the invention includes microcrystalline cellulose at about 40% wt/wt of the composition; croscarmellose sodium at about 4% wt/wt of the composition; intragranular magnesium stearate at about 0.37% wt/wt of the composition; intragranular anhydrous lactose at about 54 to about 55% wt/wt of the composition; intragranular micronized edetate calcium disodium hydrous at about 0.10% wt/wt of the composition; and intragranular micronized sodium thiosulfate pentahydrate at about 0.5% wt/wt of the composition.

In another embodiment, the composition can further contain intragranular microcrystalline cellulose at about 40% wt/wt of the composition; intragranular croscarmellose sodium at about 2% wt/wt of the composition; intragranular magnesium stearate at about 0.19% wt/wt of the composition; intragranular anhydrous lactose at about 54 to about 55% wt/wt of the composition; intragranular micronized edetate calcium disodium hydrous at about 0.10% wt/wt of the composition; and intragranular micronized sodium thiosulfate pentahydrate at about 0.5% wt/wt of the composition. The composition can further contain extragranular croscarmellose sodium at about 2% wt/wt of the composition and extragranular magnesium stearate at about 0.19% wt/wt of the composition.

In a further embodiment, the composition of the present invention provides about 0.15% wt/wt micronized tanaproget, about 40% wt/wt microcrystalline cellulose, about 54.87% wt/wt anhydrous lactose, about 4% wt/wt croscarmellose sodium, about 0.38% wt/wt magnesium stearate, about 0.1% wt/wt micronized EDTA, and about 0.5% wt/wt micronized sodium thiosulfate pentahydrate.

In still another embodiment, the composition of the present invention provides about 0.23% wt/wt micronized tanaproget, about 40% wt/wt microcrystalline cellulose, about 54.79% wt/wt anhydrous lactose, about 4% wt/wt croscarmellose sodium, about 0.38% wt/wt magnesium stearate, about 0.1% wt/wt micronized EDTA, and about 0.5% wt/wt micronized sodium thiosulfate pentahydrate.

In a further embodiment, the composition of the present invention provides about 0.31% wt/wt micronized tanaproget, about 40% wt/wt microcrystalline cellulose, about 54.71% wt/wt anhydrous lactose, about 4% wt/wt croscarmellose sodium, about 0.38% wt/wt magnesium stearate, about 0.1% wt/wt micronized EDTA, and about 0.5% wt/wt micronized sodium thiosulfate pentahydrate.

In still another embodiment, the composition of the present invention provides about 0.46% wt/wt micronized tanaproget, about 40% wt/wt microcrystalline cellulose, about 54.56% wt/wt anhydrous lactose, about 4% wt/wt croscarmellose sodium, about 0.38% wt/wt magnesium stearate, about 0.1% wt/wt micronized EDTA, and about 0.5% wt/wt of micronized sodium thiosulfate pentahydrate.

Without limitation as to the method of preparation of a composition of the invention, an example of a suitable micronized tanaproget composition is provided in Table 1.

TABLE 1

| | Component | % wt/wt |
|---|---|---|
| Intragranular | micronized tanaproget | 0.1546 |
| | MCC | 40.00 |
| | anhydrous lactose | 54.8706 |
| | EDTA | 0.10 |
| | micronized sodium thiosulfate pentahydrate | 0.5 |
| | micronized croscarmellose sodium | 2.00 |
| | magnesium stearate | 0.1875 |
| Extragranular | croscarmellose sodium | 2.00 |
| | magnesium stearate | 0.1875 |

Still a further example of a suitable micronized tanaproget composition is provided in Table 2.

TABLE 2

| | Component | % wt/wt |
|---|---|---|
| Intragranular | micronized tanaproget | 0.2316 |
| | MCC | 40.00 |
| | anhydrous lactose | 54.7935 |
| | EDTA | 0.10 |
| | micronized sodium thiosulfate pentahydrate | 0.5 |
| | micronized croscarmellose sodium | 2.00 |
| | magnesium stearate | 0.1875 |
| Extragranular | croscarmellose sodium | 2.00 |
| | magnesium stearate | 0.1875 |

Another example of a suitable micronized tanaproget composition is provided in Table 3.

TABLE 3

| | Component | % wt/wt |
|---|---|---|
| Intragranular | micronized tanaproget | 0.3088 |
| | MCC | 40.00 |
| | anhydrous lactose | 54.7163 |
| | EDTA | 0.10 |
| | micronized sodium thiosulfate pentahydrate | 0.5 |
| | micronized croscarmellose sodium | 2.00 |
| | magnesium stearate | 0.1875 |
| Extragranular | croscarmellose sodium | 2.00 |
| | magnesium stearate | 0.1875 |

Yet a further example of a suitable micronized tanaproget composition is provided in Table 4.

TABLE 4

| | Component | % wt/wt |
|---|---|---|
| Intragranular | micronized tanaproget | 0.4632 |
| | MCC | 40.00 |
| | anhydrous lactose | 54.5619 |
| | EDTA | 0.10 |
| | micronized sodium thiosulfate pentahydrate | 0.5 |
| | micronized croscarmellose sodium | 2.00 |
| | magnesium stearate | 0.1875 |
| Extragranular | croscarmellose sodium | 2.00 |
| | magnesium stearate | 0.1875 |

The composition of the invention is prepared by mixing micronized tanaproget, microcrystalline cellulose, croscarmellose sodium, micronized sodium thiosulfate pentahydrate, anhydrous lactose, micronized edetate calcium disodium hydrous, and magnesium stearate. In one embodiment, the composition is prepared by wet mixing the components therein with water. The components of the composition can also be in extragranular or intragranular forms, as determined by one of skill in the art and the requirements of the process.

A variety of apparatuses can be utilized to perform the process of the invention and includes bags of small, medium, and large sizes, screens of varying sizes, and blenders, among others.

The process can also include compacting and/or milling the composition, typically using compactors and mills selected by one of skill in the art. The milling step is typically performed on particles of varying sizes, i.e., large particles, powders, and fine powders to obtain a preferred and more uniform particle size. The milling can include several separating, recycling, and screening steps to obtain the desired particle sizes. Drying is generally performed using suitable drying instrument selected by one of skill in the art such as a fluid bed dryer.

In a further embodiment, the compositions of the present invention can be prepared by diluting the compositions with excipients. Useful excipients for dilution include those set forth below and can include MCC, croscarmellose sodium, and magnesium stearate.

Compositions containing lesser amounts of tanaproget can be prepared according to the present invention by diluting compositions containing greater amounts of tanaproget. In one embodiment, a composition containing 0.01 mg of tanaproget is prepared by diluting a composition containing 0.1, 0.15, 0.2, or 0.3 mg of tanaproget, and desirably by diluting a composition containing 0.10 mg. In another embodiment, a composition containing 0.1 mg of tanaproget is prepared by diluting a composition containing 0.15, 0.2, or 0.3 mg of tanaproget. In yet a further embodiment, a composition containing 0.15 mg tanaproget is prepared by diluting a composition containing 0.2 or 0.3 mg of tanaproget. In still another embodiment, a composition containing 0.2 mg of tanaproget is prepared by diluting a composition containing 0.3 mg of tanaproget. In another embodiment, the compositions of the invention prepared by diluting compositions containing higher amounts of tanaproget are diluted with MCC, croscarmellose sodium, magnesium stearate, and lactose.

In one embodiment, the compositions of the present invention contain particles of an optimal size to permit dissolution of the composition, e.g., the particles are less than or equal to about 100 μm. The sizes of the particles of the composition are typically measured by passing the solid composition through screens of varying sizes. In one embodiment, about 36% of the particles are greater than or equal to about 180 μm. In another embodiment, about 46% of the particles are greater than or equal to about 125 μm. In a further embodiment, about 75% of the particles are greater than or equal to about 45 μm. In still another embodiment, about 25% of the particles are less than about 45 μm.

If the particles of the compositions are larger than the optimal size and if the same have not yet been encapsulated in a capsule, the same can be subject to further milling and screening steps, among others, to reduce the particle size.

The process typically includes compressing the composition into a form suitable for oral administration and is typically a tablet or caplet. When compressed into a tablet or caplet, one of skill in the art would readily be able to select a suitable tablet or caplet press for use in the present invention. One example of such a press includes the Stokes® B2 Tablet Press, among others.

The tablet prepared according to the present invention can be optionally encapsulated in a capsule. In one embodiment, the capsule is a hydroxypropyl methylcellulose (hypromellose) capsule. The capsule can be optionally sealed with the tablet therein or a filler can be added to the capsule containing tablet. In one embodiment, the filler includes extragranular croscarmellose sodium and magnesium stearate. In a further embodiment, the tablet is placed in the capsule prior to adding the filler.

Optionally, the tablets or caplets are film-coated. Suitable film-coatings are known to those of skill in the art. For example, the film-coating can be selected from among suitable polymers such as hydroxypropylmethylcellulose, ethyl cellulose, polyvinyl alcohol, and combinations thereof. Other suitable film-coatings can be readily selected by one of skill in the art. In one embodiment, the tablet or caplet is coated with an Opadry™ seal coat. In a further embodiment, the tablet or caplet is coated with an Opadry™ Blue seal coat. Where applied, the weight percent of the film coat is generally in the range of 2% wt/wt to 6% wt/wt of the tablet or caplet. In one embodiment, the weight percent of the film coat is about 3.5% wt/wt of the tablet or caplet. Drying of the coating is accomplished by conventional means, e.g., with a fluid bed dryer.

When prepared according to the present invention, the tablets, caplets, capsules, or tablets-in-capsules containing the composition release about 86 to about 99% of tanaproget after about 90 minutes. In a further embodiment, 85% of the tanaproget, or about 90%, is released in about 15 minutes.

B. Stability of the Compositions of the Invention

The compositions of the present invention are stable over a period of about 1 month for samples stored at varying temperatures and humidities. The term stable as used herein refers to the compositions of the invention which degrade less than about 3%. Typically, it is the tanaproget that degrades in the composition. In one embodiment, the compositions are stable at about 20° C./50% relative humidity to about 45° C./75% relative humidity. In another embodiment, the compositions of the invention degrade less than about 3% over a period of greater than 1 month at temperatures at or greater than about 25° C. and a relative humidity at or greater than about 60%.

The compositions of the invention can be stored at reduced temperatures, and in one embodiment, at temperatures of about 5° C. The compositions can also be stored in the absence of water, air, and moisture. However, storage at room temperature, among other atmospheric conditions, does not affect the overall stability of the compositions.

C. Additional Components of the Compositions of the Invention

Other suitable components can be added to the compositions of the present invention, provided that the same is not already present, and will be readily apparent to one of skill in the art. Typically, the additional components are inert and do not interfere with the function of the required components of the compositions. The compositions of the present invention can thereby further include other adjuvants, syrups, elixirs, diluents, binders, lubricants, surfactants, granulating agents, disintegrating agents, emollients, metal chelators, pH adjustors, surfactants, fillers, disintegrants, and combinations thereof, among others.

Adjuvants can include, without limitation, flavoring agents, coloring agents, preservatives, and supplemental antioxidants, which can include ascorbic acid, butylated hydroxytoluene (BHT) and butylated hydroxyanisole (BHA).

Binders can include, without limitation, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone.

Lubricants can include light anhydrous silicic acid, talc, stearic acid, sodium lauryl sulfate, magnesium stearate and sodium stearyl furamate, among others. In one embodiment, the lubricant is magnesium stearate.

Granulating agents can include, without limitation, silicon dioxide, starch, calcium carbonate, pectin, crospovidone, and polyplasdone, among others.

Disintegrating agents or disintegrants can include starch, carboxymethylcellulose, substituted hydroxypropylcellulose, sodium bicarbonate, calcium phosphate, calcium citrate, sodium starch glycolate, pregelatinized starch or crospovidone, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing tanaproget to about 4 to about 6. In one embodiment, the pH of a solution containing tanaproget is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Additional fillers that can be used in the composition of the present invention include mannitol, calcium phosphate, pregelatinized starch, or sucrose.

D. Methods of Using the Compositions

The invention further provides a method of delivering tanaproget to a patient, where the method includes administering a micronized tanaproget dosing unit according to the invention.

The dosage requirements of tanaproget may vary based on the severity of the symptoms presented and the particular subject being treated. Treatment can be initiated with small dosages less than the optimum dose of tanaproget. Thereafter the dosage is increased until the optimum effect under the circumstances is reached. Precise dosages will be determined by the administering physician based on experience with the individual subject treated. In general, the compositions of this invention are most desirably administered at a concentration that will generally afford effective results without causing any unacceptable harmful or deleterious side effects. For example, an effective amount of micronized tanaproget is generally, e.g., about 1 mg, about 0.15 mg, about 0.2 mg, or about 0.3 mg.

These compositions containing micronized tanaproget are therefore useful in contraception and hormone replacement therapy. The compositions are also useful in contraception and the treatment and/or prevention of uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors, and in the preparation of medicaments useful therefor. Additional uses of the compositions include stimulation of food intake.

The compositions of the invention are formed into a suitable dosing unit for delivery to a patient. Suitable dosing units include oral dosing units, such as a directly compressible tablets, caplets, capsules, powders, suspensions, microcapsules, dispersible powders, granules, suspensions, syrups, elixirs, and aerosols. In one embodiment, the compositions of the present invention are compressed into a tablet or caplet, which is optionally added to a capsule, or the compositions are added directly to a capsule. The compositions of the invention can also be formulated for delivery by other suitable routes. These dosing units are readily prepared using the methods described herein and those known to those of skill in the art.

Solid forms, including tablets, caplets, and capsules containing micronized tanaproget can be formed by dry blending tanaproget with the components described above. In one embodiment, the capsules utilized in the present invention include hydroxypropyl methylcellulose (hypromellose) capsule, or a hard shell gelatin capsule. In another embodiment the tablets or caplets of the present invention that contain tanaproget are film-coated. Suitable film-coatings are known to those of skill in the art. For example, the film-coating can be selected from among polymers such as hydroxypropylmethylcellulose, ethyl cellulose, polyvinyl alcohol, and combinations thereof. More desirable tablet or caplet weights include tablets or caplets of about 100 mg, about 150 mg, about 200 mg, or about 300 mg. However, tablets or caplets of lesser or greater weights can be utilized as determined by one of skill in the art.

A pharmaceutically effective amount of tanaproget can vary depending on the components of the composition, mode of delivery, severity of the condition being treated, the patient's age and weight, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. Daily dosages can also be lowered or raised based on the periodic delivery.

It is contemplated that when the compositions of this invention are used for contraception or hormone replacement therapy, they can be administered in conjunction with one or more other progesterone receptor agonists, estrogen receptor agonists, progesterone receptor antagonists, and selective estrogen receptor modulators, among others.

When utilized for treating neoplastic disease, carcinomas, and adenocarcinomas, they can be administered in conjunction with one or more chemotherapeutic agents, which can readily be selected by one of skill in the art.

E. Kits of the Invention

The present invention also provides kits or packages containing micronized tanaproget. Kits of the present invention can include tanaproget and a carrier suitable for administration to a mammalian subject as discussed above. In one embodiment, the tablets, caplets, or capsules are packaged in blister packs, and in a further embodiment, Ultrx™ 2000 blister packs.

The kits or packages containing the compositions of the present invention are designed for use in the regimens described herein. In one embodiment, these kits are designed for daily oral delivery over 21-day, 28-day, 30-day, or 31-day cycles, among others, or for one oral delivery per day. When the compositions are to be delivered continuously, a package or kit can include the composition in each tablet or caplet. When the compositions of the present invention are to be delivered with periodic discontinuation, a package or kit can include placebos on those days when the composition is not delivered.

Additional components may be co-administered with the composition of the invention and include progestational agents, estrogens, and selective estrogen receptor modulators.

In one embodiment, the kits are organized to indicate a single oral formulation or combination of oral formulations to be taken on each day of the cycle, in a further embodiment including oral tablets or caplets to be taken on each of the days specified, and in still a further embodiment one oral tablet or caplet will contain each of the combined daily dosages indicated.

In one embodiment, a kit can include a single phase of a daily dosage of the composition of the invention over a 21-day, 28-day, 30-day, or 31-day cycle. Alternatively, a kit can include a single phase of a daily dosage of the composition of the invention over the first 21 days of a 28-day, 30-day, or 31-day cycle. A kit can also include a single phase of a daily dosage of the composition of the invention over the first 28 days of a 30-day or 31-day cycle.

In a further embodiment, a kit can include a single combined phase of a daily dosage of the composition of the invention and a progestational agent over a 21-day, 28-day, 30-day, or 31-day cycle. Alternatively, a kit can include a single combined phase of a daily dosage of the composition of the invention and a progestational agent over the first 21 days of a 28-day, 30-day, or 31-day cycle. A kit can also include a single combined phase of a daily dosage of the composition of the invention and a progestational agent over the first 28 days of a 30-day or 31-day cycle.

In another embodiment, a 28-day kit can include a first phase of from 14 to 28 daily dosage units of the composition of the invention; a second phase of from 1 to 11 daily dosage units of a progestational agent; and, optionally, a third phase of an orally and pharmaceutically acceptable placebo for the remaining days of the cycle.

In yet a further embodiment, a 28-day kit can include a first phase of from 14 to 21 daily dosage units of the composition of the invention; a second phase of from 1 to 11 daily dosage units of a progestational agent; and, optionally, a third phase of an orally and pharmaceutically acceptable placebo for the remaining days of the cycle.

In another embodiment, a 28-day kit can include a first phase of from 18 to 21 daily dosage units of the composition of the invention; a second phase of from 1 to 7 daily dose units of a progestational agent; and, optionally, an orally and pharmaceutically acceptable placebo for each of the remaining 0 to 9 days in the 28-day cycle.

In yet a further embodiment, a 28-day kit can include a first phase of 21 daily dosage units of the composition of the invention; a second phase of 3 daily dosage units for days 22 to 24 of a progestational agent; and, optionally, a third phase of 4 daily units of an orally and pharmaceutically acceptable placebo for each of days 25 to 28.

In another embodiment, a 28-day kit can include a first phase of from 14 to 21 daily dosage units of a progestational agent equal in progestational activity to about 35 to about 150 μg levonorgestrel, a second phase of from 1 to 11 daily dosage units of the composition of the invention; and optionally, a third phase of an orally and pharmaceutically acceptable placebo for the remaining days of the cycle in which no antiprogestin, progestin or estrogen is administered.

In a further embodiment, a 28-day kit can include a first phase of from 14 to 21 daily dosage units of a progestational agent equal in progestational activity to about 35 to about 100 μg levonorgestrel; a second phase of from 1 to 11 daily dosage units of the composition of the invention; and optionally, a third phase of an orally and pharmaceutically acceptable placebo for the remaining days of the cycle in which no antiprogestin, progestin or estrogen is administered.

In one embodiment, the daily dosage of tanaproget remains fixed in each particular phase in which it is delivered. In a further embodiment, the daily dose units described are to be delivered in the order described, with the first phase followed in order by the second and third phases. To help facilitate compliance with each regimen, in a further embodiment the kits contain the placebo described for the final days of the cycle.

A number of packages or kits are known in the art for the use in dispensing pharmaceutical agents for oral use. In one embodiment, the package has indicators for each day of the 28-day cycle, and in a further embodiment is a labeled blister package, dial dispenser package, or bottle.

The kit can further contain instructions for administering the tanaproget compositions of the present invention.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of Micronized Tanaproget

Tanaproget was prepared according to US Patent Application Publication No. 2005/0272702, published Dec. 8, 2005, was milled using a U-10 Comil mill and thereby micronized using a MC50 Jetpharma Micronizer with a EZFH-1.4 Feeder. Particle size was tested periodically for a particle size of less than about 15 μm, and desirably less than about 10 μm, being distributed throughout 50% of the sample. The micronized tanaproget was packed in triple poly-bagged fiber drums. A desiccant was inserted between the outermost bags and the atmosphere in the bags replaced with nitrogen gas.

Example 2

Preparation of Compositions and Tablets Containing Micronized Tanaproget

This example provides the preparation of tablets containing micronized tanaproget using the components of Table 5.

TABLE 5

| Component | Function | Specification |
|---|---|---|
| Micronized tanaproget | Active ingredient | In-house |
| Microcrystalline Cellulose | Filler, Granulation aid, Disintegrant | NF |
| Anhydrous Lactose | Filler | NF |
| Sodium thiosulfate pentahydrate | Antioxidant | USP |
| Edetate Calcium Disodium Hydrous | Antioxidant | USP |
| Croscarmellose Sodium | Disintegrant | NF |
| Magnesium Stearate | Lubricant | NF/EP |
| Opadry ™ II Blue | Coating material | In-house |

Tablets containing micronized tanaproget were prepared according to the following granulation. See, Table 6. If the total wt/wt % of the components exceeded 100%, the amount of anhydrous lactose was adjusted by reducing or increasing the amount of anhydrous lactose in the composition.

TABLE 6

| | Tablet Strength (mg) | | | | | | | |
|---|---|---|---|---|---|---|---|---|
| | 100 | | 150 | | 200 | | 300 | |
| Component | Amount (mg) | % wt/wt | Amount (mg) | % wt/wt | Amount (mg) | % wt/wt | Amount (mg) | % wt/wt |
| Intragranular | | | | | | | | |
| Micronized tanaproget | 0.1051 | 0.1546 | 0.1575 | 0.2316 | 0.210 | 0.3088 | 0.315 | 0.4632 |
| MCC | 27.20 | 40.00 | 27.20 | 40.00 | 27.20 | 40.00 | 27.20 | 40.00 |
| Anhydrous lactose | 37.312 | 54.8706 | 37.260 | 54.7935 | 37.207 | 54.7163 | 37.102 | 54.5619 |
| EDTA | 0.068 | 0.10 | 0.068 | 0.10 | 0.068 | 0.10 | 0.068 | 0.10 |
| micronized sodium thiosulfate pentahydrate | 0.34 | 0.5 | 0.34 | 0.5 | 0.34 | 0.5 | 0.34 | 0.5 |
| micronized croscarmellose sodium | 1.36 | 2.00 | 1.36 | 2.00 | 1.36 | 2.00 | 1.36 | 2.00 |
| magnesium stearate | 0.1275 | 0.1875 | 0.1275 | 0.1875 | 0.1275 | 0.1875 | 0.1275 | 0.1875 |
| Extragranular | | | | | | | | |
| Croscarmellose sodium | 1.36 | 2.00 | 1.36 | 2.00 | 1.36 | 2.00 | 1.36 | 2.00 |
| Magnesium stearate | 0.1275 | 0.1875 | 0.1275 | 0.1875 | 0.1275 | 0.1875 | 0.1275 | 0.1875 |
| Total (Core Tablet Weight) | 68.00 | 100.00 | 68.00 | 100.00 | 68.00 | 100.00 | 68.00 | 100.00 |
| Opardy II Blue | 2.38 | 3.5 | 2.38 | 3.5 | 2.38 | 3.5 | 2.38 | 3.5 |
| Purified Water* | — | qs | — | qs | — | qs | — | qs |

*Not present in final dosage form.

Microcrystalline Cellulose (MCC) and anhydrous lactose were mixed in a suitable size PK-Blender equipped with intensifier bar for 1 minute without activating the intensifier bar. A second portion of anhydrous lactose was added to a canister and the canister was rotated for 1 minute to dust the walls of the canister with the anhydrous lactose. Micronized tanaproget, sodium thiosulfate and EDTA were added to the canister and mixed for 1 minute. The content of the canister was then emptied into the PK-blender. A portion of anhydrous lactose was used to rinse the emptied canister for 1 minute and was then transferred to the PK-blender. Croscarmellose sodium was added to the PK-blender. The remaining MCC and anhydrous lactose were added to the PK-blender. The blender was mixed, for a certain amount of time at an appropriate mixing speed, depending on the size of the blender, with and without the intensifier bar [e.g., 20 revolutions per minute (rpm) for 13 minutes with intensifier bar inactivated, followed by 4 minutes with the intensifier bar activated, and followed by 1 minute with the intensifier bar inactivated]. Intragranular magnesium stearate was added to the PK-Blender and mixed for 2 minutes without the intensifier bar activated. The blend from step 8 was discharged from the PK Blender into a double poly-lined container. The blend was then compacted and milled using an Alexanderwerk roller compactor. The milled material was transferred to a suitable size PK-Blender and mixed for 1 minute. Extragranular croscarmellose sodium was added to the PK-blender and mixed for 10 minutes without the intensifier bar activated. Extragranular magnesium stearate was added to the blender and mixed for 2 minutes without the intensifier bar activated. The blend was discharged from the PK-blender into a tarred double poly-lined container. The tablets were thereby prepared by compressing the final blend into 68 mg tablets using a rotary tablet press equipped with 7/32" (0.2187") round modified concave tooling.

The tablets were coated using a film coat suspension by first preparing an Opadry™ II Blue suspension by slowly adding the Opadry™ II Blue to water with continuous agitation. The tablets were loaded into an appropriate size pan of a coating machine and a sufficient film-coat suspension was applied to provide around 3.5% average dry-coat weight per tablet.

Example 3

Variation of MCC, Croscarmellose Sodium, and Magnesium Stearate Concentrations in Tanaproget Compositions In this Example, ten (10) compositions containing tanaproget, EDTA, sodium thiosulfate, anhydrous lactose and varying amounts of MCC, croscarmellose sodium, and magnesium stearate were prepared according to the procedure set forth in Example 2 and using the components set forth in Tables 7 and 8. The remaining portion of the composition was adjusted using anhydrous lactose to obtain a total % wt/wt of 100 as noted in Table 8.

TABLE 7

| Component | % wt/wt |
|---|---|
| Micronized tanaproget | 0.1546 |
| EDTA | 0.10 |
| micronized sodium thiosulfate pentahydrate | 0.5 |
| Purified Water* | qs |

*Not present in final dosage form.

TABLE 8

| | | % wt/wt | | |
|---|---|---|---|---|
| Run | MCC | Croscarmellose Sodium | Magnesium Stearate | Anhydrous Lactose |
| 1 | 40 | 4 | 0.375 | 54.87 |
| 2 | 30 | 6 | 0.5 | 62.745 |
| 3 | 50 | 2 | 0.5 | 46.745 |
| 4 | 50 | 6 | 0.5 | 42.745 |
| 5 | 30 | 2 | 0.5 | 66.745 |
| 6 | 30 | 6 | 0.25 | 63.0 |
| 7 | 50 | 6 | 0.25 | 43.0 |
| 8 | 40 | 4 | 0.375 | 54.87 |
| 9 | 50 | 2 | 0.25 | 47.0 |
| 10 | 30 | 2 | 0.25 | 77.0 |

Example 4

Variation of Excipient Concentration in Tanaproget Compositions

In this Example, twelve (12) compositions containing fixed amounts of tanaproget and EDTA and varying amounts of MCC, croscarmellose sodium, magnesium stearate, sodium thiosulfate, anhydrous lactose, and cysteine were prepared using the components set forth in Table 9 and the procedure set forth below.

50% of the MCC and 40% of the anhydrous lactose were passed through a #40 mess screen, transferred to a PK-Blender, and mixed for 1 minute. 10% of the lactose was added to a bag and mixed with sodium thiosulfate, cysteine, and EDTA, passed through a #40 mesh screen and added to the PK blender containing the MCC. Tanaproget was added to another bag, mixed, passed through a #40 mesh screen, and added to the PK blender. 10% of the lactose was passed through a #40 screen, used to rinse the bag that contained the tanaproget, and added to the PK-blender. The croscarmellose sodium was passed through a #40 screen and added to the blender. The remaining MCC and lactose were also passed through a #40 screen and added to the blender.

The material in the blender was blended for 12 minutes without the intensifier bar, followed by 3 minutes with the intensifier bar, and then an additional 1 minute without the intensifier bar. Magnesium stearate was passed through a #40 screen, added to the blender, and mixed. The blend from the PK-blender was then roller compacted and milled using an Alexanderwerk roller compactor and mill running.

The compacted and milled granulation was transferred to a PK-blender and mixed. Extragranular croscarmellose sodium was passed through a #40 mesh screen, added to the PK blender, and mixed. Extragranular magnesium stearate was passed through a #40 mesh screen, added to the PK-blender, and mixed to form the final blend.

The blend was compressed into 68 mg tablets using an instrumented Korsh XL100 tablet press with 7/32" modified concave B tooling. The tablets were also coated with a 20% Opadry II blue dispersion.

TABLE 9

| | Run (% wt/wt) | | | | | |
|---|---|---|---|---|---|---|
| Component | 1 | 2 | 3 | 4 | 5 | 6 |
| Intragranular | | | | | | |
| Micronized tanaproget | 0.1545 | 0.1545 | 0.1545 | 0.1545 | 0.1545 | 0.1545 |
| MCC | 40.00 | 30.00 | 50.00 | 50.00 | 30.00 | 30.00 |
| Anhydrous lactose | 54.3705 | 62.2455 | 46.2455 | 42.2455 | 66.2455 | 62.4955 |
| micronized L-cysteine | 0.50 | 0.50 | 0.50 | 0.50 | 0.50 | 0.50 |
| micronized EDTA | 0.10 | 0.10 | 0.10 | 0.10 | 0.10 | 0.10 |
| Disodium thiosulfate | 0.50 | 0.50 | 0.50 | 0.50 | 0.50 | 0.50 |
| Croscarmellose sodium | 2.00 | 3.00 | 1.00 | 3.00 | 1.00 | 3.00 |
| Magnesium stearate | 0.188 | 0.25 | 0.25 | 0.25 | 0.25 | 0.125 |
| Extragranular | | | | | | |
| Croscarmellose sodium | 2.00 | 3.00 | 1.00 | 3.00 | 1.00 | 3.00 |
| Magnesium stearate | 0.187 | 0.25 | 0.25 | 0.25 | 0.25 | 0.125 |
| Opadry Blue | — | — | — | — | — | — |

TABLE 9-continued

| Component | Run (% wt/wt) | | | | | |
|---|---|---|---|---|---|---|
| | 7 | 8 | 9 | 10 | 11 | 12 |
| Intragranular | | | | | | |
| Micronized tanaproget | 0.1545 | 0.1545 | 0.1545 | 0.1545 | 0.1545 | 0.1545 |
| MCC | 50.00 | 40.00 | 50.00 | 30.00 | 40.00 | 40.00 |
| Anhydrous lactose | 42.4955 | 54.3705 | 46.4955 | 66.4955 | 54.9205 | 53.8205 |
| micronized L-cysteine | 0.50 | 0.50 | 0.50 | 0.50 | 0.25 | 0.75 |
| micronized EDTA | 0.10 | 0.10 | 0.10 | 0.10 | 0.10 | 0.10 |
| Disodium thiosulfate | 0.50 | 0.50 | 0.50 | 0.50 | 0.25 | 0.75 |
| Croscarmellose sodium | 3.00 | 2.00 | 1.0 | 1.00 | 2.00 | 2.00 |
| Magnesium stearate | 0.125 | 0.188 | 0.125 | 0.125 | 0.188 | 0.188 |
| Extragranular | | | | | | |
| Croscarmellose sodium | 3.00 | 2.00 | 1.00 | 1.00 | 2.00 | 2.00 |
| Magnesium stearate | 0.125 | 0.187 | 0.125 | 0.125 | 0.187 | 0.187 |
| Opadry Blue | — | 3.00 | — | — | 3.00 | 3.00 |

Example 5

Variation of Antioxidant Concentrations in Tanaproget Compositions

In this Example, three (3) compositions containing micronized tanaproget, MCC, croscarmellose sodium, and magnesium stearate and varying amounts of sodium thiosulfate and EDTA were prepared according to the procedure set forth in Example 2 and using the components set forth in Tables 10 and 11. The remaining portion of the composition was adjusted using anhydrous lactose to obtain a total % wt/wt of 100 as noted in Table 11.

TABLE 10

| Component | % wt/wt |
|---|---|
| Micronized tanaproget | 0.1546 |
| MCC | 40 |
| magnesium stearate | 0.375 |
| croscarmellose sodium | 4 |
| Purified Water* | qs |

*Not present in final dosage form.

TABLE 11

| | % wt/wt | | |
|---|---|---|---|
| Run | Sodium Thiosulfate | EDTA | Anhydrous Lactose |
| 1 | 0.25 | 0.05 | 55.17 |
| 2 | 0.5 | 0.1 | 54.87 |
| 3 | 0.75 | 0.15 | 54.57 |

All documents listed in this specification and priority applications including U.S. patent application Ser. No. 12/752,520, filed Apr. 1, 2010, U.S. patent application Ser. No. 11/411,523, filed Apr. 26, 2006, and U.S. Provisional Patent Application No. 60/675,550, filed Apr. 28, 2005 are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A kit comprising a pharmaceutical composition comprising an intragranulation comprising micronized tanaproget or a pharmaceutically acceptable salt thereof, microcrystalline cellulose, croscarmellose sodium, anhydrous lactose, magnesium stearate, micronized edetate calcium disodium hydrous, and micronized sodium thiosulfate pentahydrate.

2. The kit according to claim 1, wherein said pharmaceutical composition further comprises extragranular croscarmellose sodium and extragranular magnesium stearate.

3. The kit according to claim 2, wherein said extragranular croscarmellose sodium comprises about 2% wt/wt of said pharmaceutical composition.

4. The kit according to claim 2, wherein said extragranular magnesium stearate comprises about 0.19% of said pharmaceutical composition.

5. The kit according to claim 1, wherein the particles of said micronized tanaproget are less than about 10 µm.

6. The kit according to claim 1, wherein the particles of said micronized sodium thiosulfate pentahydrate are less than about 31 µm.

7. The kit according to claim 1, wherein the particles of said micronized sodium edetate calcium disodium hydrous are less than about 35 µm.

8. The kit according to claim 1, wherein said pharmaceutical composition degrades less than about 3% over a period of greater than 1 month at temperatures at or greater than about 25° C. and a relative humidity at or greater than about 60%.

9. The kit according to claim 1, wherein said tanaproget comprises about 0.15% to about 0.50% wt/wt of said pharmaceutical composition.

10. The kit according to claim 1, wherein said tanaproget comprises about 0.15% wt/wt of said pharmaceutical composition.

11. The kit according to claim 1, wherein said tanaproget comprises about 0.23% wt/wt of said pharmaceutical composition.

12. The kit according to claim 1, wherein said tanaproget comprises about 0.31% wt/wt of said pharmaceutical composition.

13. The kit according to claim 1, wherein said tanaproget comprises about 0.5% wt/wt of said pharmaceutical composition.

14. The kit according to claim 1, wherein said intragranular microcrystalline cellulose comprises about 40% wt/wt of said pharmaceutical composition.

15. The kit according to claim 1, wherein said intragranular croscarmellose sodium comprises about 2% wt/wt of said pharmaceutical composition.

16. The kit according to claim 1, wherein said intragranular magnesium stearate comprises about 0.19% wt/wt of said pharmaceutical composition.

17. The kit according to claim 1, wherein said intragranular anhydrous lactose comprises about 54% to about 55% wt/wt of said pharmaceutical composition.

18. The kit according to claim 1, wherein said intragranular micronized edetate calcium disodium hydrous comprises about 0.10% wt/wt of said pharmaceutical composition.

19. The kit according to claim 1, wherein said intragranular micronized sodium thiosulfate pentahydrate comprises about 0.5% wt/wt of said pharmaceutical composition.

20. The kit according to claim 1, wherein the particles of said pharmaceutical composition are less than about 100 μm.

21. The kit according to claim 1, further comprising one or more progestational agent, estrogen, or selective estrogen receptor modulator.

22. The kit according to claim 1, comprising a single phase of a daily dosage of said pharmaceutical composition over a 21-day, 28-day, 30-day, or 31-day cycle.

23. The kit according to claim 1, comprising a single phase of a daily dosage of said pharmaceutical composition over the first 21 days of a 28-day, 30-day, or 31-day cycle.

24. The kit according to claim 1, comprising a single phase of a daily dosage of said pharmaceutical composition over the first 28 days of a 30-day or 31-day cycle.

25. The kit according to claim 1, comprising a single combined phase of a daily dosage of said pharmaceutical composition and a progestational agent;
wherein the daily dosage units total 28.

26. The kit according to claim 1, comprising 21 daily dosage units of a single combined phase of said pharmaceutical composition and a progestational agent;
wherein the daily dosage units total 28, 30, or 31.

27. The kit according to claim 1, comprising 28 daily dosage units of a single combined phase of said pharmaceutical composition and a progestational agent;
wherein the daily dosage units total 30 or 31.

28. The kit according to claim 1, comprising:
(i) a first phase of from 14 to 28 daily dosage units of said pharmaceutical composition;
(ii) a second phase of from 1 to 11 daily dosage units of a progestational agent; and
(iii) daily dosage units of an orally and pharmaceutically acceptable placebo;
wherein the daily dosage units total 28.

29. The kit according to claim 1, comprising:
(i) a first phase of from 14 to 21 daily dosage units of said pharmaceutical composition; and
(ii) a second phase of from 1 to 11 daily dosage units of a progestational agent; and
(iii) daily dosage units of an orally and pharmaceutically acceptable placebo;
wherein the daily dosage units total 28.

30. The kit according to claim 1, comprising:
(i) a first phase of from 18 to 21 daily dosage units of said pharmaceutical composition; and
(ii) a second phase of from 1 to 7 daily dose units of a progestational agent; and
(iii) daily dosage units of an orally and pharmaceutically acceptable placebo;
wherein the daily dosage units total 28.

31. The kit according to claim 1, comprising:
(i) a first phase of 21 daily dosage units of said pharmaceutical composition;
(ii) a second phase of 3 daily dosage units for days 22 to 24 of a progestational agent;
(iii) a third phase of 4 daily dosage units for days 25 to 28 of a pharmaceutically acceptable placebo;
wherein the daily dosage units total 28.

32. The kit according to claim 1, comprising:
(i) a first phase of from 14 to 21 daily dosage units of a progestational agent equal in progestational activity to about 35 to about 150 μg levonorgestrel; and
(ii) a second phase of from 1 to 11 daily dosage units of said pharmaceutical composition; and
(iii) daily dosage units of an orally and pharmaceutically acceptable placebo;
wherein the daily dosage units total 28.

33. The kit according to claim 1, comprising:
(i) a first phase of from 14 to 21 daily dosage units of a progestational agent equal in progestational activity to about 35 to about 100 μg levonorgestrel; and
(ii) a second phase of from 1 to 11 daily dosage units of said pharmaceutical composition; and
(iii) daily dosage units of an orally and pharmaceutically acceptable placebo;
wherein the daily dosage units total 28.

34. The kit according to claim 1, which is designed for treating or preventing benign prostatic hypertrophy, benign neoplastic disease, malignant neoplastic disease, dysfunctional bleeding, uterine leiomyomata, polycystic ovary syndrome, carcinomas, or adenocarcinomas.

35. A kit comprising a pharmaceutical composition comprising about 0.15% wt/wt micronized tanaproget or a pharmaceutically acceptable salt thereof, about 40% wt/wt microcrystalline cellulose, about 4% wt/wt croscarmellose sodium, about 54.87% wt/wt anhydrous lactose, about 0.38% wt/wt magnesium stearate, about 0.1% wt/wt micronized edetate calcium disodium hydrous, and about 0.5% wt/wt micronized sodium thiosulfate pentahydrate.

36. A kit comprising a pharmaceutical composition comprising about 0.23% wt/wt micronized tanaproget or a pharmaceutically acceptable salt thereof, about 40% wt/wt microcrystalline cellulose, about 4% wt/wt croscarmellose sodium, about 54.79% wt/wt anhydrous lactose, about 0.38% wt/wt magnesium stearate, about 0.1% wt/wt micronized edetate calcium disodium hydrous, and about 0.5% wt/wt micronized sodium thiosulfate pentahydrate.

37. A kit comprising a pharmaceutical composition comprising about 0.31% wt/wt micronized tanaproget or a pharmaceutically acceptable salt thereof, about 40% wt/wt microcrystalline cellulose, about 4% wt/wt croscarmellose sodium, about 54.71% wt/wt anhydrous lactose, about 0.38% wt/wt magnesium stearate, about 0.1% wt/wt micronized edetate calcium disodium hydrous, and about 0.5% wt/wt micronized sodium thiosulfate pentahydrate.

38. A kit comprising a pharmaceutical composition comprising about 0.46% wt/wt micronized tanaproget or a pharmaceutically acceptable salt thereof, about 40% wt/wt microcrystalline cellulose, about 4% wt/wt croscarmellose sodium, about 54.56% wt/wt anhydrous lactose, about 0.38% wt/wt magnesium stearate, about 0.1% wt/wt micronized edetate calcium disodium hydrous, and about 0.5% wt/wt micronized sodium thiosulfate pentahydrate.

* * * * *